United States Patent
Imai

(10) Patent No.: US 11,653,965 B2
(45) Date of Patent: May 23, 2023

(54) TOOL FOR BONE PLATE BENDING, TOOL SET FOR BONE PLATE BENDING, AND METHOD FOR BENDING BONE PLATE

(71) Applicant: MEIRA Corporation, Nagoya (JP)

(72) Inventor: Takahiro Imai, Seki (JP)

(73) Assignee: MEIRA CORPORATION, Nagoya (JP)

( * ) Notice: Subject to any disclaimer, the term of this patent is extended or adjusted under 35 U.S.C. 154(b) by 80 days.

(21) Appl. No.: 17/148,897

(22) Filed: Jan. 14, 2021

(65) Prior Publication Data

US 2021/0220033 A1    Jul. 22, 2021

(30) Foreign Application Priority Data

Jan. 17, 2020   (JP) .............................. JP2020-006310

(51) Int. Cl.
*A61B 17/88* (2006.01)
*A61B 17/56* (2006.01)
*A61B 17/80* (2006.01)

(52) U.S. Cl.
CPC .......... *A61B 17/8863* (2013.01); *A61B 17/80* (2013.01); *A61B 2017/564* (2013.01)

(58) Field of Classification Search
CPC ........................... A61B 17/8019; A61B 17/808
See application file for complete search history.

(56) References Cited

U.S. PATENT DOCUMENTS 4,187,840 A * 2/1980 Watanabe .......... A61B 17/8866
606/86 R

FOREIGN PATENT DOCUMENTS

JP          4071563 B2      4/2008
JP          2014113365 A    6/2014
WO    WO-2007092441 A2 *  8/2007    ......... A61B 17/1728

* cited by examiner

*Primary Examiner* — Anu Ramana
(74) *Attorney, Agent, or Firm* — Buchanan Ingersoll & Rooney PC

(57) ABSTRACT

A bone plate bending tool includes a substantially rod-shaped first member having a first sandwiching surface, a substantially rod-shaped second member slidable along a side part of the first member and having a second sandwiching surface, and a connection tubular member connected to the second member and enclosing a peripheral surface of the first member. A projection on one of the sandwiching surfaces is insertable into a through-hole of the bone plate and does not prevent the bone plate from being sandwiched between the sandwiching surfaces. The connection tubular member is axially movable on the peripheral surface of the first member while the second member is disposed on the first member's side part. The connecting tubular member that has moved axially forward restricts expansion between the sandwiching surfaces. The sandwiching surfaces, together with the forward-moved connecting tubular member, sandwich and immovably hold a peripheral edge of the bone plate through-hole.

7 Claims, 11 Drawing Sheets

TOOL FOR BONE PLATE BENDING, TOOL SET FOR BONE PLATE BENDING, AND METHOD FOR BENDING BONE PLATE

BACKGROUND OF THE INVENTION

Field of the Invention

The present invention relates to a tool for bending the bone plate, a set of the tool for bending the bone plate, and a method for bending a bone plate.

Description of the Related Arts

When a person breaks her/his end portion of bone (distal end portion and proximal end portion) such as thigh bone, fibula, tibia, humerus, radius, and ulna or in the vicinity of the end portion of the bone, there may be a case in which a lot of bone fragments are necessary to be joined with the bone body to regain an original state. In the treatment of the fracture portion, after the position and postures of bone fragments are restored, the bone fragments and the bone body are fixed to each other. Thus, a bone plate to be mounted on the bone fragments and on the bone body crosslinkingly is used.

The bone is different in its configuration in dependence on a patient. In a clinic scene, it is necessary to bend a bone plate produced in a predetermined configuration in advance to in conformity to the configuration of a portion (fracture portion) where the bone fragments are to be mounted. As the bone plate, metal plates tough, light, and highly biosafe are often used. When a doctor bends the bone plate, a bending tool is utilized.

The following tools for bending a bone joining plate are disclosed in Japanese Patent Application Laid-Open Publication No. 2014-113365 (patent document 1) and Japanese patent No. 4071563 (patent document 2). The tool disclosed in the above-described patent documents 1 and 2 have the two receiving parts disposed at an interval in such a way as to support the bone joining plate and the pressing part which is disposed between the receiving parts and moves therebetween. The bone joining plate supported between the receiving parts is bent by pressing the bone joining plate with the bone joining plate being sandwiched between the receiving parts and the pressing part.

The tools for bending the bone joining plate described in the patent documents 1 and 2 necessitate an operator to grip the grip part (manual operation part) to hold the bone joining plate. Thus, if the operator loosens the force to grip the grip part during operation, the bone joining plate shifts or drops out. That is, the operator cannot bend the bone joining plate as desired.

The bone plate has holes for allowing drills and pins to penetrate therethrough. But the hole may be distorted while the bone joining plate is being bent.

SUMMARY OF THE INVENTION

It is an object of the present invention to provide a tool for bending the bone plate, a set of the tool for bending the bone plate, and a method for bending a bone plate.

In order to achieve the above-described object, the following is provided.

A tool for bending a bone plate having a through-hole comprises a substantially rod-shaped first member having a first sandwiching surface on a front end surface of said first member; a substantially rod-shaped second member, which slides along a side part of said first member and has a second sandwiching surface positioned in front of said first sandwiching surface and opposed to said first sandwiching surface, a connection tubular member connected to said second member and enclosing a peripheral surface of said first member, a projection provided on one of said first sandwiching surface and said second sandwiching surface, and said projection is capable of inserting into said through-hole of said bone plate and does not prevent said bone plate from being pinchingly sandwiched between said first sandwiching surface and said second sandwiching surface, wherein said connection tubular member is axially movable on said peripheral surface of said first member in a state said second member being disposed on said side part of said first member, said connecting tubular member that has moved forward in an axial direction restricts an expansion between said first sandwiching surface and said second sandwiching surface, and said first sandwiching surface and said second sandwiching surface, in cooperation with said connecting tubular member that has moved forward in said axial direction, pinchingly sandwich and immovably hold a peripheral edge of said through-hole of said bone plate into which said projection has inserted.

A tool for bending a bone plate having a through-hole comprises a substantially rod-shaped first member having a first sandwiching surface on a front end surface of said first member; a substantially rod-shaped second member, which slides along a side part of said first member and has a second sandwiching surface positioned in front of said first sandwiching surface and opposed to said first sandwiching surface, a connection tubular member connected to said second member and enclosing a peripheral surface of said first member, a projection provided on one of said first sandwiching surface and said second sandwiching surface, and said projection is capable of inserting into said through-hole of said bone plate and does not prevent said bone plate from being pinchingly sandwiched between said first sandwiching surface and said second sandwiching surface, wherein said second member has a second member-side threadedly engaging portion provided at an outer side surface of a rear end portion of said second member, said connection tubular member has a tubular member-side threadedly engaging portion which is provided at an inner surface of said connection tubular member and screws with said second member-side threadedly engaging portion, and said connecting tubular member moves toward a distal end of said first member by rotating said connecting tubular member in a predetermined direction, said connection tubular member has a contact portion which contacts said first member when moved toward said distal end of said first member by rotating said connecting tubular member in a predetermined direction, and said contact portion contacted said first member restrict an expansion between said first sandwiching surface and said second sandwiching surface.

A set of a tool for bending a bone plate comprises a tool for bending said bone plate and a gripping tool having a gripping portion capable of gripping said bone plate at a portion other than a portion where said bone plate is pinchingly held by said bone plate bending tool and a substantially rod-shaped main body.

Method for bending a bone plate using said bone plate bending tool includes, preparing said bone plate bending tool; allowing said projection of said bone plate bending tool to insert to said through-hole of said bone plate; holding and pinching said bone plate between said first sandwiching surface and said second sandwiching surface; and curvingly deforming said bone plate at portions other than a portion where said bone plate is pinchingly held between said first and second sandwiching surfaces with said bone plate being gripped with an operator's hand or a jig.

DETAILED DESCRIPTION OF THE PREFERRED EMBODIMENTS

Figure 1:
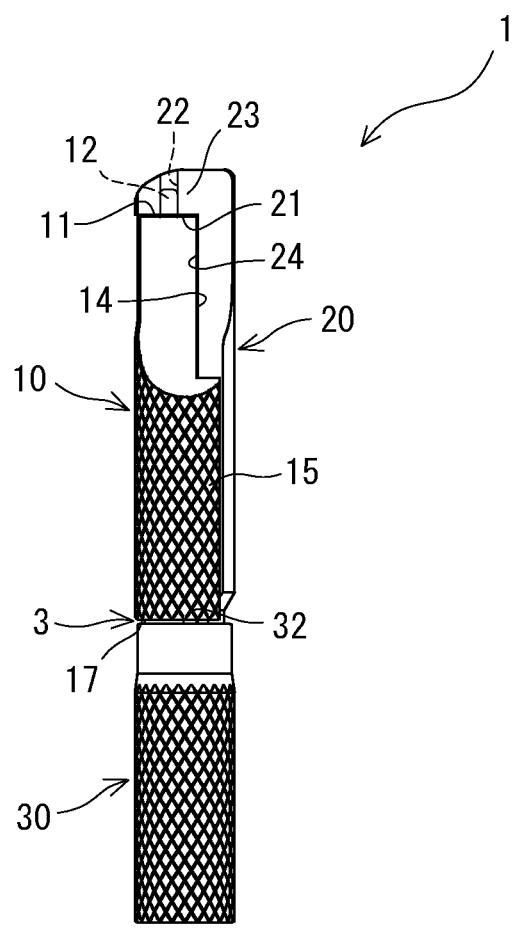
FIG. 1 is a front view showing an embodiment of a tool for bending a bone plate.

The tool of the present invention for bending a bone plate is described below by using embodiments shown in the drawings. In this embodiment, a vertical direction FIG. 1 may be sometimes described as a front-rear direction. In addition, an upper side and a lower side may sometimes be described as a front-end side and rear-end side respectively.

As shown in FIGS. 1 through 6, a tool 1 for bending bone plate (in many cases, hereinafter referred to as merely bone plate bending tool 1) has a first sandwiching surface 11, a second sandwiching surface 21 opposed to the first sandwiching surface 11 and capable of moving close thereto and apart therefrom, and a projection 12 provided either on the first sandwiching surface 11 or on the second sandwiching surface 21 (in this embodiment, provided on the first sandwiching surface 11), capable of penetrating through a through-hole 51 formed on the bone plate 5 and not preventing the bone plate 5 from being held by a pinching force between the first sandwiching surface 11 and the second sandwiching surface 21. Both the first sandwiching surface 11 and the second sandwiching surface 21 have a sandwiching holding mechanism 3 for holding a state in which a sandwiching force is applied to a peripheral portion of the through-hole 51 with the projection 12 in penetration through the through-hole 51.

Also as shown in FIGS. 1 through 6, a tool 1 for bending a bone plate having a through-hole of the present invention has a substantially rod-shaped first member 10 having a first sandwiching surface 11 on a front end surface of the first member 10; a substantially rod-shaped second member 20, which slides along a side part of the first member 10 and has a second sandwiching surface 21 positioned in front of the first sandwiching surface 11 and opposed to the first sandwiching surface 11, a connection tubular member 30 connected to the second member 20 and enclosing a peripheral surface of the first member 10, a projection 12 provided on one of the first sandwiching surface 11 and the second sandwiching surface 21, and the projection 12 is capable of inserting into the through-hole 51 of the bone plate 5 and does not prevent the bone plate 5 from being pinchingly sandwiched between the first sandwiching surface 11 and the second sandwiching surface 21, wherein the connection tubular member 30 is axially movable on the peripheral surface of the first member 10 in a state the second member 20 being disposed on the side part of the first member 10, the connecting tubular member 30 that has moved forward in an axial direction restricts an expansion between the first sandwiching surface 11 and the second sandwiching surface 21, and the first sandwiching surface 11 and the second sandwiching surface 21, in cooperation with the connecting tubular member 30 that has moved forward in the axial direction, pinchingly sandwich and immovably hold a peripheral edge of the through-hole 51 of the bone plate 5 into which the projection 12 has inserted.

Also as shown in FIGS. 1 through 6, a tool 1 for bending a bone plate having a through-hole of the present invention has a substantially rod-shaped first member 10 having a first sandwiching surface 11 on a front end surface of the first member 10; a substantially rod-shaped second member 20, which slides along a side part of the first member 10 and has a second sandwiching surface 21 positioned in front of the first sandwiching surface 11 and opposed to the first sandwiching surface 11, a connection tubular member 30 connected to the second member 20 and enclosing a peripheral surface of the first member 10, a projection 12 provided on one of the first sandwiching surface 11 and the second sandwiching surface 21, and the projection 12 is capable of inserting into the through-hole 51 of the bone plate 5 and does not prevent the bone plate 5 from being pinchingly sandwiched between the first sandwiching surface 11 and the second sandwiching surface 21, wherein the second member 20 has a second member-side threadedly engaging portion 26 provided at an outer side surface of a rear end portion of the second member 20, the connection tubular member 30 has a tubular member-side threadedly engaging portion 31 which is provided at an inner surface of the connection tubular member 30 and screws with the second member-side threadedly engaging portion 26, and the connecting tubular member 30 moves toward a distal end of the first member 10 by rotating the connecting tubular member 30 in a predetermined direction, the connection tubular member 30 has a contact portion 32 which contacts the first member 10 when moved toward the distal end of the first member 10 by rotating the connecting tubular member 30 in a predetermined direction, and the contact portion 32 contacted the first member 10 restrict an expansion between the first sandwiching surface 11 and the second sandwiching surface 21.

As shown in FIGS. 1 through 6, the bone plate bending tool 1 of this embodiment has a substantially rod-shaped first member 10 having the first sandwiching surface 11 on its front end surface (upper-side end surface in FIG. 1); a substantially rod-shaped second member 20 positioned in front of (upper side in FIG. 1) of the first sandwiching surface 11, having the second sandwiching surface 21 opposed to the first sandwiching surface 11, and sliding along a side part of the first sandwiching surface 11; and a connection tubular member 30 connected to the second member 20 with the second member 20 being disposed on the side part of the first member 10, enclosing a peripheral surface 13 of a rear-end portion of the first member 10, and being movable on the peripheral surface 13 in the axial direction (vertical direction in FIG. 1) of the first member 10. The connection tubular member 30 is movable in the axial direction of the first member 10. The connection tubular member 30 which has moved in the axial direction of the first member 10 prevents the first member 10 from moving rearward (downward in FIG. 1) and is capable of holding the state in which the bone plate 5 is pinchingly held between the first sandwiching surface 11 and the second sandwiching surface 21. The projection 12 provided either on the first sandwiching surface 11 or on the second sandwiching surface 21 (in this embodiment, the projection 12 is provided on the first sandwiching surface 11) is capable of penetrating into the through-hole 51 formed on the bone plate 5 and does not prevent the bone plate 5 from being held by the pinching force between the first sandwiching surface 11 and the second sandwiching surface 21.

In the bone plate bending tool 1, one of the first sandwiching surface 11 and the second sandwiching surfaces 21 (the second sandwiching surface 21 in this embodiment) has a hole portion 22 capable of accommodating the projection 12.

The bending tool for the bone plate 5 of the embodiment shown in FIGS. 1 through 6 has the substantially rod-shaped first member 10 and the substantially rod-shaped second member 20, and the connection tubular member 30.

More specifically, the first member 10 which is a substantially rod-shaped member extending in the front-rear direction of the bone plate bending tool 1 is made by machining a round rod-shaped metal material. A front-end side portion of the first member 10 becomes gradually narrower in its width (dimension in a left-right direction in FIG. 2) toward its front end. A front-end surface of the first member 10 forms the first sandwiching surface 11. The round rod-shaped (sectionally circular) projection 12 projects forward from the first sandwiching surface 11. An outer peripheral surface (the surface on which an operator touches when the operator uses the bone plate bending tool 1) of a central portion of the first member 11 is subjected to knurling (not shown in a sectional view), e.g. non-slip processing or the like to improve operability in bending processing.

A smooth sliding surface 14 is formed on the side part of the first member 10 [the side (right side in FIGS. 1 and 4) where the second member 20 is disposed] by extending the smooth sliding surface 14 in the axial direction of the first member 10. Projected portions (side guide) 15, 15 are formed at central portions of the first member 10 by projecting the projected portions 15, 15 in such a way as to pinchingly sandwich the sliding surface 14 therebetween. The projected portions (side guide) 15, 15 function as a guide in axially displacing (sliding in the axial direction) the first member 10 and the second member 20 relative to each other to move the first sandwiching surface 11 and the second sandwiching surface 21 close to each other and apart from each other. In this embodiment, the sliding surface 14 extends from a proximal end of the side part of the first member 10 to a front end of the side part thereof. The sliding surface 14 is formed as a flat surface.

An accommodation concave portion 16 capable of accommodating an urging means (coil spring 40) which will be described later is provided at a rear-end side part of the first member 10. The accommodation concave portion 16 is open toward the second member 20 at the side part of the first member 10 and open rearward at a rear-end portion thereof. The rear-end side part of the first member 10 is formed almost cylindrically. The side part of the rear-end side part of the first member 10 is open. Thus, the rear-end side part of the first member 10 has a configuration of a gutter partly open in its side part. The rear-end side part of the first member 10 is set smaller in its diameter than the central portion (the above-described knurled portion) thereof and can be enclosed by the connection tubular member 30 which will be described later. A stepped portion 17 is formed at the boundary between the rear-end side part (the above-described smaller diameter portion) of the first member 10 and the central portion (the above-described knurled portion) of the first member 10. The rear-end portion (the portion positioned at the side rearward from the rear-end side part of the first member 10 set smaller than the central portion thereof in the diameter thereof) of the first member 10 is set smaller in its diameter than the rear-end side part thereof to prevent an outer peripheral surface 13 of the first member 10 from interfering with a tubular member-side threadedly engaging portion 31 which will be described later.

Figure 2:
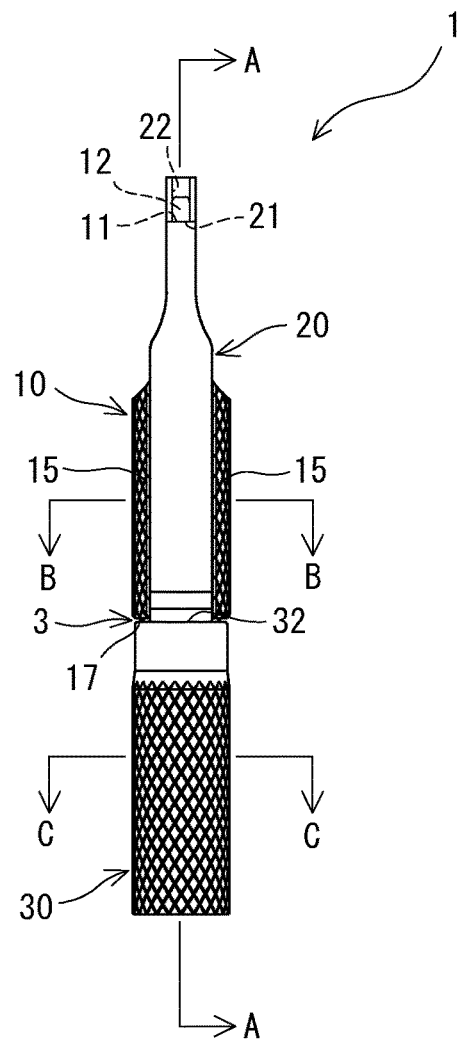
FIG. 2 is a right-side view showing the embodiment of the bending tool of the present invention for the bone plate.
Figure 3:
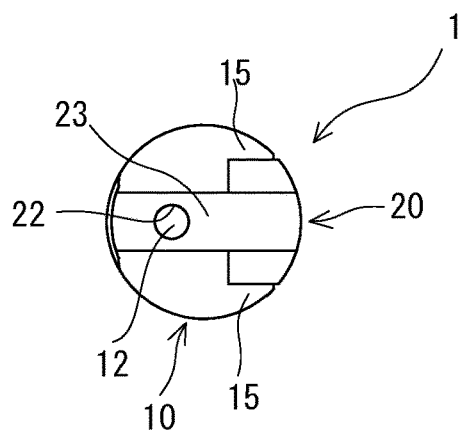
FIG. 3 is a plan enlarged explanatory diagram showing the embodiment of the bending tool of the present invention for the bone plate.

The second member 20 is a substantially rod-shaped member extending in the front-rear direction of the bone plate bending tool 1 and is made by machining a rod-shaped metal material. As shown in FIG. 2, a front-end side portion of the second member 20 becomes gradually narrower in its width (dimension in the left-right direction in FIG. 2) toward its front end. The width of a front-end portion of the second member 20 is set almost equally to that of the front-end portion of the above-described first member 10. An upper projected portion 23 projecting toward the first member 10 is formed at the front-end portion of the second member 20. A substantially flat surface exposed toward the rear of the upper projected portion 23 forms a second sandwiching surface 21. The second sandwiching surface 21 is positioned at the front of the first sandwiching surface 11 with the second sandwiching surface 21 being opposed to the first sandwiching surface 11. The hole portion 22 (having an inner diameter equal to or slightly larger than the outer diameter of the projection 12) capable of accommodating the projection 12 formed on the first sandwiching surface 11 is formed on the second sandwiching surface 21. In this embodiment, the hole portion 22 penetrates the upper projected portion 23 in the front-rear direction of the bone plate bending tool. The hole portion 22 does not necessarily have to be formed as a through-hole.

The second member 20 has a smooth sliding-contact surface 24, formed at a part located at the side of the first member 10, which extends in the axial direction of the second member 20 and is opposed to the sliding surface 14 of the first member 10. A part (rear-end side part of the second member 20) of the sliding-contact surface 24 covers a side part of an opening of the accommodation concave portion 16 of the first member 10 at the side of the second member 20.

The second member 20 has a lower projected portion 25, formed at a rear-end portion of the second member 20, which projects toward the first member 10. The external form of the lower projected portion 25 is substantially equivalent to or slightly smaller than the internal form of the accommodation concave portion 16 of the first member 10, is capable of penetrating into the accommodation concave portion 16, and is movable inside the accommodation concave portion 16 in the axial direction of the first member 10. A space for accommodating the urging means (coil spring 40) which will be described later is formed among the accommodation concave portion 16 of the first member 10, the sliding-contact surface 24 of the second member 20, and the lower projected portion 25 of the second member 20.

The rear-end portion of the second member 20 has a second member-side threadedly engaging portion 26 consisting of a thread groove formed on the outer peripheral surface of the second member 20 located opposite to the first member 10. More specifically, the second member 20 has a second member-side threadedly engaging portion 26 provided at an outer side surface of a rear end portion of the second member 20. The second member-side threadedly engaging portion 26 is capable of threadedly engaging the tubular member-side threadedly engaging portion 31 formed on an inner surface of the connection tubular member 30 which will be described later. An outer surface of the rear-end portion of the first member 10 is not provided with a threadedly engageable portion (female threadedly engageable portion) of the connection tubular member 30, but is formed as a flat surface so that the outer surface of the rear-end portion of the first member 10 does not become an obstacle in the rotation of the connection tubular member 30.

The connection tubular member 30 is a substantially cylindrical member extending in the front-rear direction of the bone plate bending tool and is made by machining a rod-shaped metal material. The outer peripheral surface of the rear-end side part of the first member 10 and that of the rear-end side part of the second member 20 are enclosed in a state in which the second member 20 is disposed at the side part of the first member 10.

Figure 4:
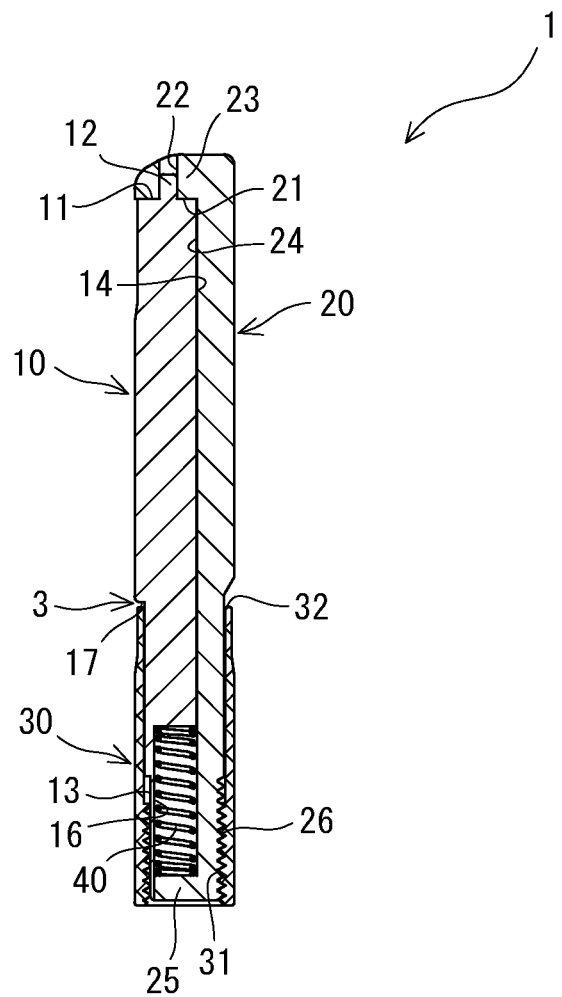
FIG. 4 is a sectional explanatory diagram taken along a line A-A of FIG. 2.
Figure 5:
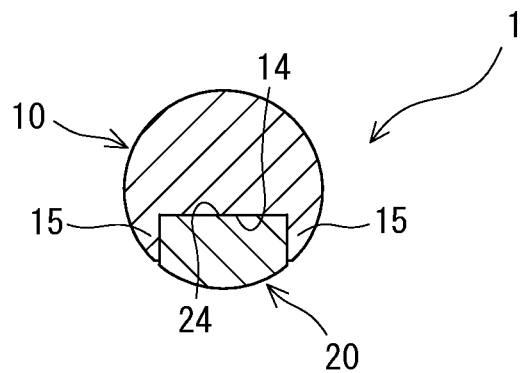
FIG. 5 is a sectional enlarged explanatory diagram taken along a line B-B of FIG. 2.
Figure 6:
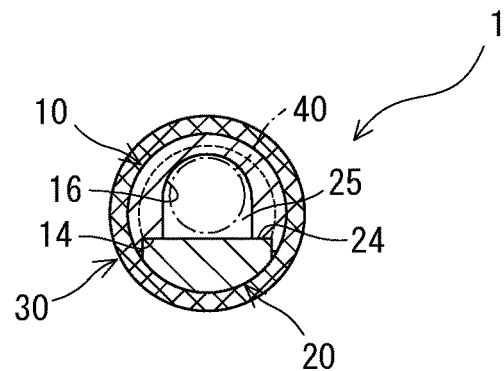
FIG. 6 is a sectional enlarged explanatory diagram taken along a line C-C of FIG. 2.

As shown in FIG. 4, the connection tubular member 30 has a tubular member-side threadedly engaging portion 31, threadedly engageable with the second member-side threadedly engaging portion 26, which is formed on the inner surface of a rear-end side part thereof. In this embodiment, the tubular member-side threadedly engaging portion 31 is formed as a screw thread (female thread). The connection tubular member 30 threadedly engages the second member-side threadedly engaging portion 26 of the second member 20 at the tubular member-side threadedly engaging portion 31. In this manner, the connection tubular member 30 is connected to the second member 20. In the bone plate bending tool 1 of this embodiment, the second member 20 has the second member-side threadedly engaging portion 26 at the rear-end portion thereof. The connection tubular member 30 has the tubular member-side threadedly engaging portion 31 on the inner surface thereof. By rotating the connection tubular member 30 in a predetermined direction, the threaded engagement between the second member-side threadedly engaging portion 26 and the tubular member-side threadedly engaging portion 31 proceeds. At this time, the connection tubular member 30 is movable toward the front end of the first member 10. In other words, the connection tubular member 30 is axially movable on the peripheral surface of the first member 10 in a state the second member 10 being disposed on the side part of the first member 10.

The front-end surface of the connection tubular member 30 is formed as a contact portion 32 capable of contacting the stepped portion 17 of the first member 10. Owing to the contact between the stepped portion 17 of the first member 10 and the contact portion 32 of the connection tubular member 30, a rearward movement of the first member 10 is prevented. That is, when the bone plate 5 is sandwiched between the first sandwiching surface 11 and the second sandwiching surface 21 owing to the axial movement of the connection tubular member 30 toward the first member 10, the connection tubular member 30 having the contact portion 32 contacts the first member 10. As a result, an expansion between the first sandwiching surface 11 and second sandwiching surface 21 is prevented. In other words, in the bone plate bending tool 1, the sandwiching holding mechanism 3 holding a state in which the bone plate 5 to be bent is pinchingly held between the first sandwiching surface 11 and the second sandwiching surface 21 is constructed by the contact between the stepped portion 17 of the first member 10 and the contact portion 32 of the connection tubular member 30 and threaded engagement between the threadedly engaging portion of the connection tubular member 30 and the threadedly engaging portion of the second member 20.

An outer peripheral surface (the surface on which the operator touches when the bone plate bending tool 1 is used) of the connection tubular member 30 is subjected to knurling (not shown in the drawings), e.g. non-slip processing or the like to improve operability in bending processing.

The bone plate bending tool 1 is formed in the shape of a substantially round rod (see FIG. 3) as a whole in its outer configuration and compact because the bone plate bending tool 1 is formed by combining the above-described first member 10, the second member 20, and the connection tubular member 30 with one another. The bone plate bending tool 1 may be provided with a rolling prevention construction (for example, projection, flat surface, and the like) on a portion and in a range which do not interfere with an operation (when the bone plate 5 is bent).

The bone plate bending tool 1 has the urging means (coil spring 40) for urging the first member 10 or/and the second member 20 in a direction in which the first sandwiching surface 11 and the second sandwiching surface 21 approach to each other.

More specifically, as shown in FIG. 4, in the bone plate bending tool 1, the coil spring 40 serving as the urging means is disposed in a space partitioned by the accommodation concave portion 16 of the first member 10, the sliding-contact surface 24, and lower projected portion 25 of the second member 20. The coil spring 40 is accommodated in the above-described space in a pre-compressed state. Thereby, the first member 10 and the second member 20 are urged relative to each other in a direction in which the first sandwiching surface 11 and the second sandwiching surface 21 approach to each other (more specifically, the first sandwiching surface 11 is urged forward, whereas the second sandwiching surface 21 is urged rearward). In other words, as shown in FIG. 4, because the second member 20 and connection tubular member 30 are connected to each other by the treaded engagement of both members, the first member 10 is in a state where the first member 10 is pressed forward by the urging member.

In the bone plate bending tool 1, the projection 12 penetrable into the through-hole 51 of the bone plate 5 is formed on the first member 10. Therefore, by penetrating the projection 12 into the through-hole 51 during the bending processing of the bone plate 5, it is possible to prevent slippage and dropout of the bone plate 5 and improve the bending processability of the bone plate 5. Further, the inner surface of the through-hole 51 is supported by the projection 12, and portions in the neighborhood of the through-hole are pinchingly sandwiched by the first sandwiching surface 11 of the first member 10 and the second sandwiching surface 21 of the second member 20, i.e., supported by both surfaces 11 and 21 disposed above and below the through-hole respectively. Thus, it is possible to prevent the through-hole 51 from being distorted by the processing of bending the bone plate 5. Supposing that a thread groove is formed on the inner surface of the through-hole 51, as a result of deformation of the through-hole 51 (thread groove) during the bending processing of the bone plate 5, there occurs a problem that a bone screw (male screw) cannot be screwed thereinto. The bone plate bending tool 1 is effective for avoiding the occurrence of such a problem.

In the bone plate bending tool 1, the second sandwiching surface 21 has the hole portion 22 capable of accommodating the projection 12 formed on the first sandwiching surface 11. Therefore, when the projection 12 is penetrated into the through-hole 51 sufficiently or penetrated therethrough, it is possible to prevent the projection 12 from interfering with the second sandwiching surface 21 and thus, avoid the occurrence of a problem that the projection 12 prevents the bone plate 5 from being held by a pinching force with the bone plate being pinchingly held between the first sandwiching surface and the second sandwiching surface. It is preferable that in a state where the bone plate 5 is not gripped by the operator, the hole portion 22 is capable of accommodating the entire projection 12. In other words, it is preferable that the first sandwiching surface 11 and the second sandwiching surface 21 are capable of contacting each other.

The bone plate bending tool 1 has the sandwiching holding mechanism 3 for holding the state of the bone plate in which the bone plate 5 to be bent is pinchingly held by the pinching force between the first sandwiching surface and the second sandwiching surface. More specifically, in the bone plate bending tool 1, the stepped portion 17 of the first member 10 contacts the contact portion 32 of the connection tubular member 30 connected to (threadedly engaged with) the second member 20. Thereby, the first member 10 is prevented from moving rearward. That is, owing to the contact between the contact portion 32 of the connection tubular member 30 and the stepped portion 17 of the first member 10 and the connection (threaded screwing) between the connection tubular member 30 and the second member 20, the expansion of the space between the first sandwiching surface 11 and the second sandwiching surface 21 is prevented. In other words, the first sandwiching surface 11 and the second sandwiching surface 21 pinchingly sandwich and immovably hold a peripheral edge of the through-hole 51 of the bone plate 5 into which the projection 12 has inserted by moving (axially moving on the peripheral surface of the first member 10) the connecting tubular member 30. Thereby it is possible to prevent the bone plate 5 sandwiched by the pinching force in a desired state between the first sandwiching surface 11 and the second sandwiching surface 21 from slipping and dropping out of place and thus, improve the bending processability of the bone plate 5. The peripheral edge of the through hole 51 of the bone plate 5 refers to a portion of the bone plate 5 forming the outer edge of the through hole 51 and a portion of the bone plate 5 existing on the outer portion of the outer edge of the through hole 51. Further, the peripheral edge of the through hole 51 of the bone plate 5 pinchingly sandwiched does not have to be the entire peripheral edge of the through hole 51 (the entire peripheral edge), but a part of the peripheral edge of the through hole 51 (for example, both sides of the peripheral portion of the through hole 51 in the longitudinal direction of the bone plate 5).

In the bone plate bending tool 1, by rotating the connection tubular member 30, the threaded engagement between the second-member side threadedly engaging portion 26 and the tubular member-side threadedly engaging portion 31 proceeds. Further, the connection tubular member 30 is movable toward the front end of the first member 10. Therefore, it is possible to finely adjust the force (pinching force) for pinchingly sandwiching the bone plate 5 between the first sandwiching surface and the second sandwiching surface.

The bone plate bending tool 1 has the coil spring 40 serving as the urging means for urging the first member 10 and the second member 20 in the direction in which the first sandwiching surface 11 and the second sandwiching surface 21 approach to each other. Thereby, while the bone plate 5 is being bent (particularly, before the bone plate 5 is held by the pinching force between the first sandwiching surface 11 and the second sandwiching surface 21), the bone plate 5 is sandwiched therebetween (temporarily sandwiched therebetween) by the urging force of the urging means without the operator applying a force to the bone plate bending tool 1. Therefore, it is possible to prevent the bone plate 5 from slipping and dropping out of place and thus improve the bending processability of the bone plate 5.

The method of the present invention for bending the bone plate is described below by using embodiments shown in FIGS. 7 through 13, and FIG. 16. Herein, the method for bending the bone plate 5 by using the above-described bone plate bending tool 1 is described below.

Figure 7:
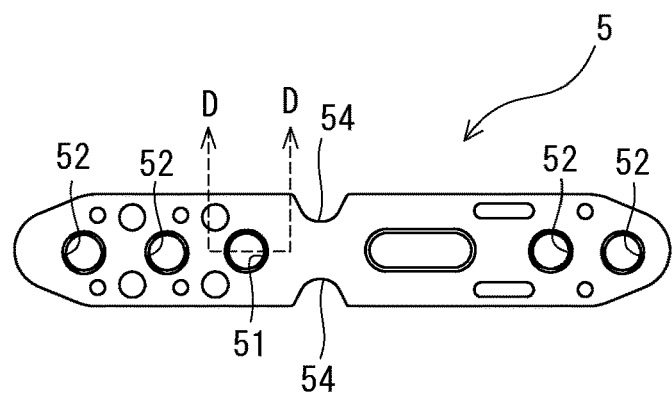
FIG. 7 is a reference example of the bone plate to be bent in the present invention.
Figure 8:
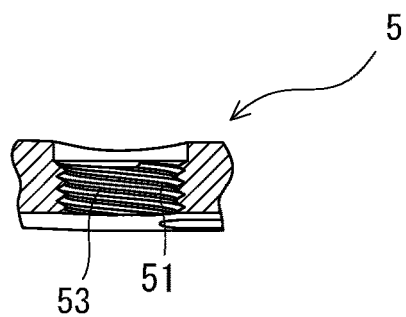
FIG. 8 is a sectional enlarged explanatory diagram taken along a line D-D of FIG. 7.

As shown in FIGS. 7 and 8, the bone plate 5 to be bent in this embodiment is substantially rectangular, flat, and has a plurality of holes. A part of the holes are through-holes 51, 52 having a thread grove 53 formed respectively on the inner surface thereof (in this embodiment, the trough-hole 51 into which the projection 12 is inserted is set to 51, whereas other through-holes are set to 52 to distinguish both of the through-holes from each other). The thread groove formed on the inner surface of each of the through-holes 51, 52 serves as means for fixing the bone screw having a screw thread (male screw) at its head to the through-hole.

Preferable examples of materials which can be used to form the bone plate 5 include titanium alloys (specifically, Ti-6A1-4V of JIST7401-2, ASTM F-136(Ti-6A1-4V ELI)), pure titanium (specifically, JIST7401-1), and stainless steel (specifically, SUS304, SUS316 of JISG4303).

A method for preparing a bone plate bending tool 1 having a projection 12, provided on either a first sandwiching surface 11 or on a second sandwiching surface 21, which is capable of penetrating into a through-hole 51 formed in penetration through a bone plate 5 provided on a first sandwiching surface 11 or a second sandwiching surface 21 opposed thereto, and which does not prevent the bone plate 5 from being pinchingly held by the pinching force between the first sandwiching surface 11 and the second sandwiching surface 21; a step of holding the bone plate 5 between the first sandwiching surface 11 and the second sandwiching surface 21 in a state in which the bone plate 5 is held by a pinching force with the projection 12 in penetration into the through-hole 51 of the bone plate 5; and a step of gripping the bone plate 5 pinchingly held by hands or a jig so as to curvingly deform the bone plate 5 at a portion other than a portion where the bone plate 5 is pinchingly held.

More specifically, initially, the above-described bone plate bending tool 1, namely, the following bone plate bending tool 1 for bending the bone plate is prepared. The bone plate bending tool 1 has the first sandwiching surface 11, the second sandwiching surface 21 opposed to the first sandwiching surface 11, and the projection 12 provided on the first sandwiching surface 11 capable of penetrating through the through-hole 51 formed on the bone plate 5 and not preventing the bone plate 5 from being pinchingly held by the pinching force between the first sandwiching surface 11 and the second sandwiching surface 21. The projection 12 is penetrable through the hole (through-hole 51), formed through the bone plate 5, which has the thread groove 53 formed on the inner surface thereof.

In the bone plate bending tool 1 prepared herein, the projection 12 is penetrable through the through-hole 51 of the bone plate 5, and the other of the first sandwiching surface 11 or the second sandwiching surface 21 (herein the second sandwiching surface 21) has the hole portion 22 capable of accommodating the projection 12 projecting from the through-hole 51.

Figure 9:
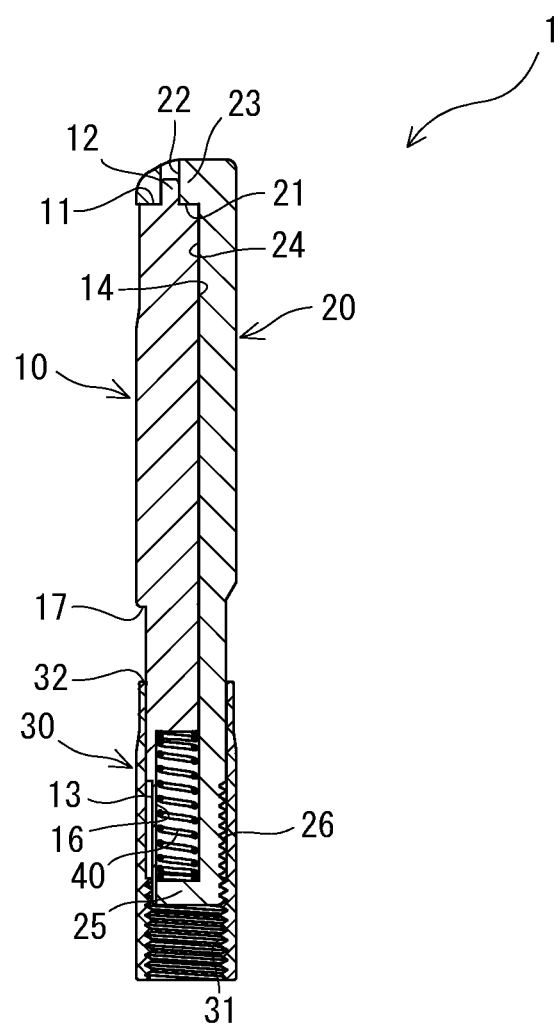
FIG. 9 is an explanatory diagram showing one step of an embodiment of a method, of the present invention, for bending a bone plate.

As shown in FIG. 9, before the bone plate 5 is disposed between the first sandwiching surface 11 and the second sandwiching surface 21, the contact between the contact portion 32 of the connection tubular member 30 and the first member 10 (stepped portion 17) is released. More specifically, by reversely rotating the connection tubular member 30, the threaded engagement between the second-member side threadedly engaging portion 26 and the tubular member-side threadedly engaging portion 31 is retreated to move the connection tubular member 30 toward the rear end of the first member 10 so that the space between the first sandwiching surface 11 and the second sandwiching surface 21 is sufficiently expanded to dispose the bone plate 5 therebetween.

Figure 10:
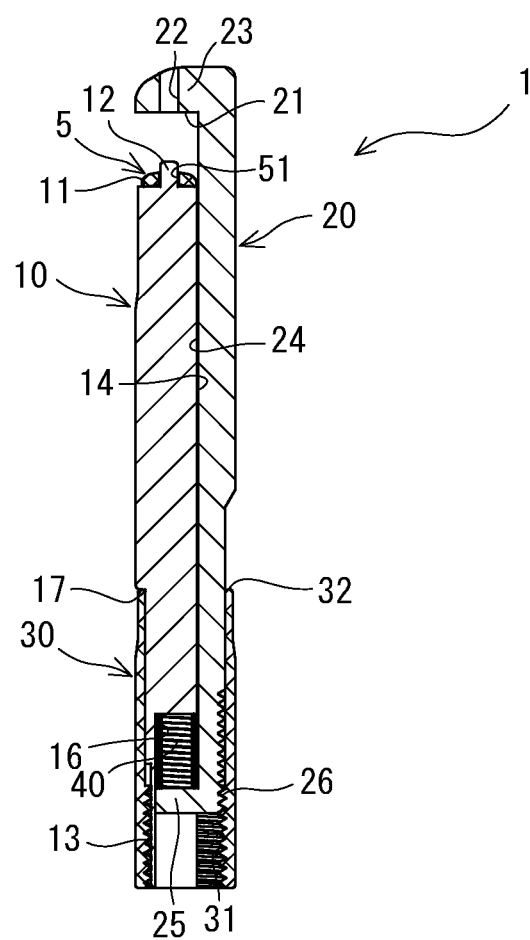
FIG. 10 is an explanatory diagram showing one step subsequent to a step shown in FIG. 9.

Thereafter as shown in FIG. 10, the bone plate 5 is disposed between the first sandwiching surface 11 and the second sandwiching surface 21. In the bone plate bending tool 1, the first member 10 and the second member 20 are urged by the urging force of the urging means (coil spring 40) in a direction in which the first sandwiching surface 11 and the second sandwiching surface 21 approach to each other. Therefore, it is necessary for the operator to expand the space between the first sandwiching surface 11 and the second sandwiching surface 21 (more specifically, the operator moves the first member 10 rearward) against the urging force of the coil spring 40. The projection 12 is penetrated into the through-hole 51 of the bone plate 5 with the space between the first sandwiching surface 11 and the second sandwiching surface 21 being sufficiently expanded to dispose the bone plate 5 therebetween.

Figure 11:
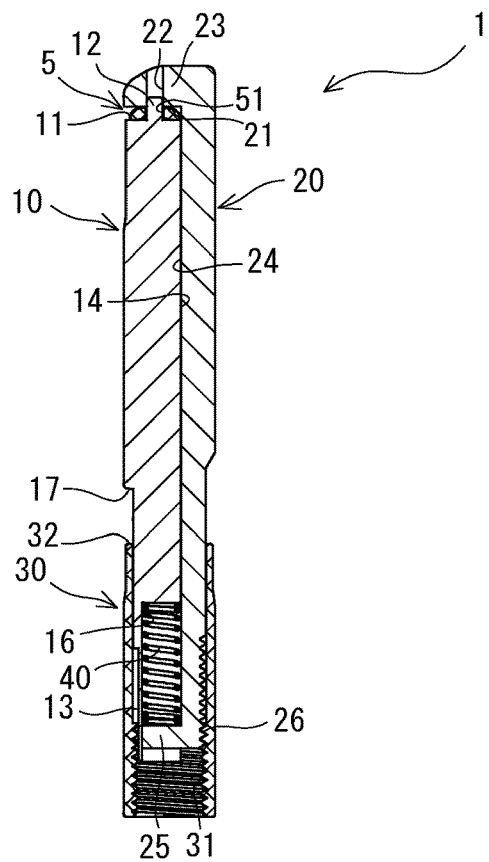
FIG. 11 is an explanatory diagram showing one step subsequent to a step shown in FIG. 10.

When the operator releases the force for expanding the first and second sandwiching surfaces (the force for moving the first member 10 rearward against the urging force of the coil spring 40) for expanding the first sandwiching surface 11 and the second sandwiching surface 21 therebetween, as shown in FIG. 11, the first and second sandwiching surfaces are urged in an approaching direction. Thereby the bone plate 5 is temporarily pinchingly held between the first sandwiching surface 11 and the second sandwiching surface 21.

Figure 12:
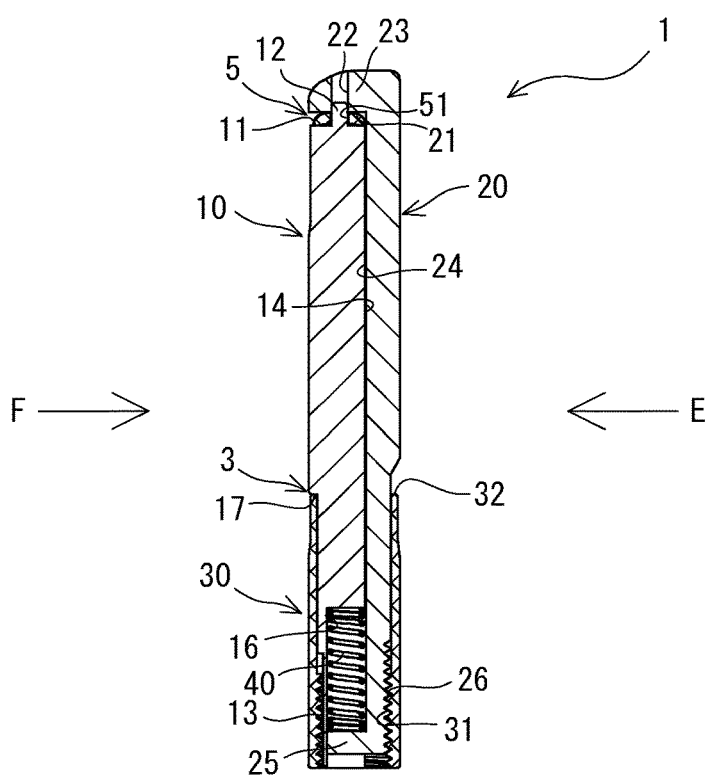
FIG. 12 is an explanatory diagram showing one step subsequent to a step shown in FIG. 11.

Thereafter as shown in FIG. 12, by rotating the connection tubular member 30, the threaded engagement between the second member-side threadedly engaging portion 26 and the tubular member-side threadedly engaging portion 31 is allowed to proceed so that the connection tubular member 30 is moved toward the front end of the first member 10. As a result of the movement of the connection tubular member 30 toward the front end of the first member 10, the contact portion 32 and the first member 10 (stepped portion 17) contact each other. Thereby, the bone plate 5 is sandwiched by the pinching force between the first sandwiching surface 11 and the second sandwiching surface 21 with the projection 12 in penetration into the through-hole 51 of the bone plate 5. By finely adjusting the movement amount (rotation amount) of the connection tubular member 30 at this time, it is possible to finely adjust the sandwiching force between the first sandwiching surface 11 and the second sandwiching surface 21. Owing to the contact between the contact portion 32 of the connection tubular member 30 and the first member 10 (stepped portion 17), the expansion between the first sandwiching surface 11 and the second sandwiching surface 21 is prevented. Thereby, the bone plate 5 is held in a state in which the bone plate 5 is kept to be sandwiched between both sandwiching surfaces 11 and 21.

Figure 13:
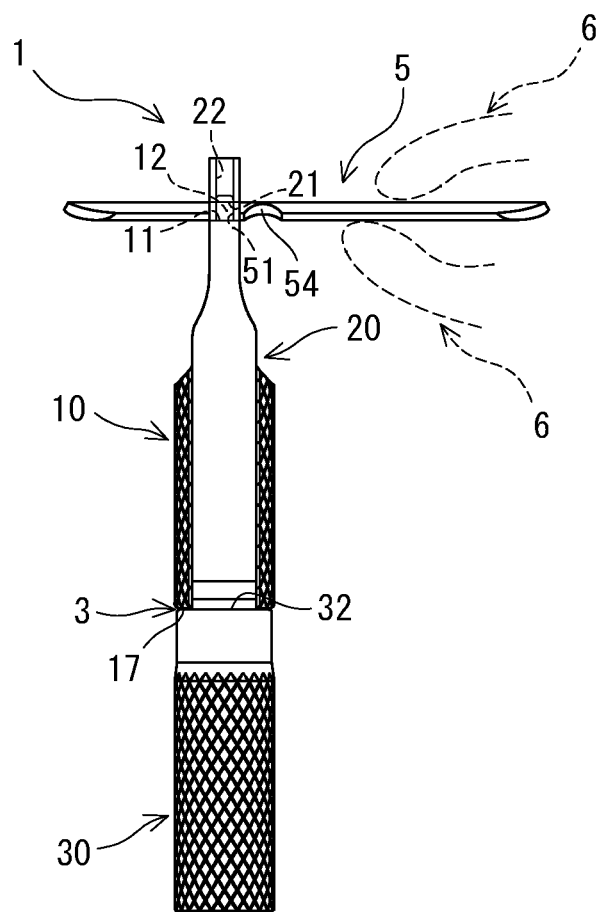
FIG. 13 is an arrow explanatory view of an E-direction shown in FIG. 12.
Figure 16:
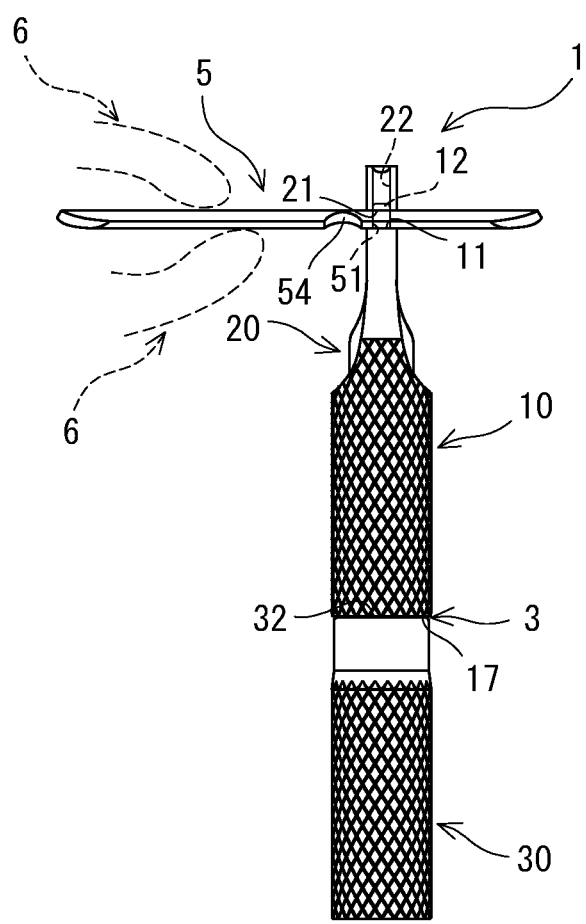
FIG. 16 is an arrow explanatory view of an F-direction shown in FIG. 12.

Thereafter as shown in FIG. 13 and FIG. 16, the bone plate 5 held in the bone plate bending tool 1 by the pinching force is gripped with the operator's hand or a jig [in this embodiment, a hand 6 (shown by a thin broken line in FIG. 13 and FIG. 16)] to curvingly deform the bone plate at a portion other than the portions (portions on the periphery of the through-hole 51) held by being sandwiched by the pinching force between both sandwiching surfaces 11 and 21. In this embodiment, a pair of cutouts 54, 54 is formed on the bone plate 5 (see FIG. 7). The strength of the portion of the bone plate 5 where the cutouts 54, 54 are formed is set lower than those of other portions of the bone plate 5. That is, the cutout-formed portions of the bone plate 5 are deformable so that the cutouts 54, 54 can be intentionally deformed on the bone plate 5.

And, as shown in FIG. 13 and FIG. 16, the peripheral edge of the through-hole 51 of the bone plate 5 into which the projection 12 has inserted (specifically, at least both sides of the bone plate 5 of the through hole 51 in the longitudinal direction) is pinchingly sandwiched between the first sandwiching surface 11 and the second sandwiching surface 21 of the tool 1. Therefore, a portion (through hole 51) of the bone plate 5 is not deformed, even if the bone plate 5 is gripped with the operator's hand or a jig [in this embodiment, a hand 6 (shown by a thin broken line in FIG. 13 and FIG. 16)] and is curvingly deformed at a portion other than the portions pinchingly sandwiched (portions on the periphery of the through-hole 51).

Figure 14:
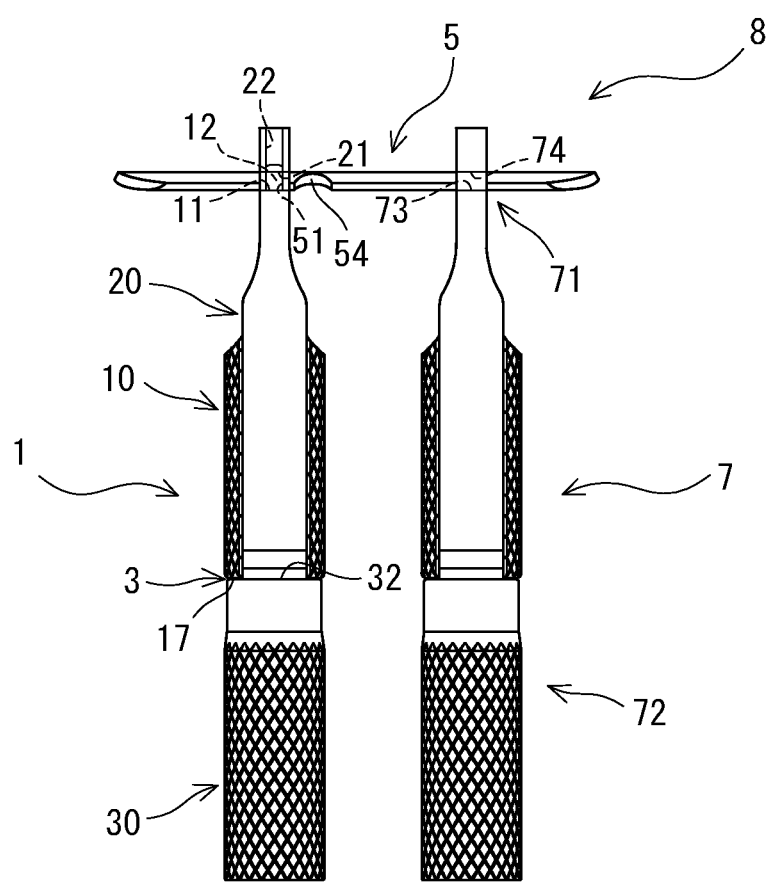
FIG. 14 is an explanatory view for explaining a use state of a bending tool set of a bone plate of an embodiment of the present invention.

As shown in FIG. 14, the bone plate bending tool 1 can be also used as a set 8 of the tool for bending the bone plate, together with a gripping tool 7 having a gripping part 71 capable of gripping the bone plate 5 at a portion other than the portion where the bone plate 5 is held by the pinching force by the bone plate bending tool 1, and a substantially rod-shaped body part 72. Except that the gripping tool 7 of this embodiment is not provided with the projection 12, the gripping tool 7 used in this embodiment has a construction equivalent to the above-described bone plate bending tool 1. That is, the gripping tool 7 of this embodiment is so constructed that a part of the bone plate 5 can be sandwiched in a region between a first sandwiching surface 73 and a second sandwiching surface 74 where an expansion amount in its front-rear direction is adjustable.

In a case where the bone plate bending tool set 8 having the above-described construction is used, by operating the body part 72 of the gripping tool 7 (the body part 72 corresponds to the first member 10, the second member 20, and the connection tubular member 30 of the bone plate bending tool 1, all of which extend below the gripping part 71 of the gripping tool 7) in bending bone plate 5, it is possible to apply a larger bending force (bending moment)

to the bone plate 5 as compared with the case in which only the bone plate bending tool 1 is used. Thus, it is possible to achieve the processing of the bending the bone plate 5 more easily. The gripping tool 7 may not have the above-described sandwiching holding mechanism (construction for maintaining the held state of the bone plate by the contact between the connection tubular member and the first member) or the urging means (coil spring). The gripping part 71 of the gripping tool 7 may be so constructed as to fix a predetermined expansion amount of the gap between the first sandwiching surface 73 and the second sandwiching surface 74 in advance.

In the bone plate bending tool 1, the projection 12 may be formed on the second sandwiching surface 21, while the hole portion 22 may be formed on the first sandwiching surface 11. Because in the bone plate bending tool 1, the bone plate can be temporarily held by penetrating the projection 12 into the through-hole 51 of the bone plate 5, it is preferable that the projection 12 is formed on the first sandwiching surface 11 or the second sandwiching surface 21 which is disposed on the lower side (rearward side) when the bone plate bending tool 1 is used.

The bone plate bending tool 1 may not be provided with the hole portion 22. For example, in a case where the projection 12 is shorter than the thickness of the bone plate 5 to be bent, the projection 12 does not project from the other side of the through-hole 51 when the projection penetrates thereinto. Therefore, it does not occur that the projection 12 prevents the bone plate 5 from being held with the bone plate 5 being sandwiched by the pinching force between the first sandwiching surface 11 and the second sandwiching surface 21.

As the urging means, the coil spring 40 is not limitedly used, but it is possible to appropriately use springs having other forms (for example, leaf spring, disc spring or the like) and known elastic bodies (for example, urethane or the like). The urging means can be used not only in spaces formed inside the bone plate bending tool 1, but also at portions exposed to the outside of the bone plate bending tool 1.

Figure 15:
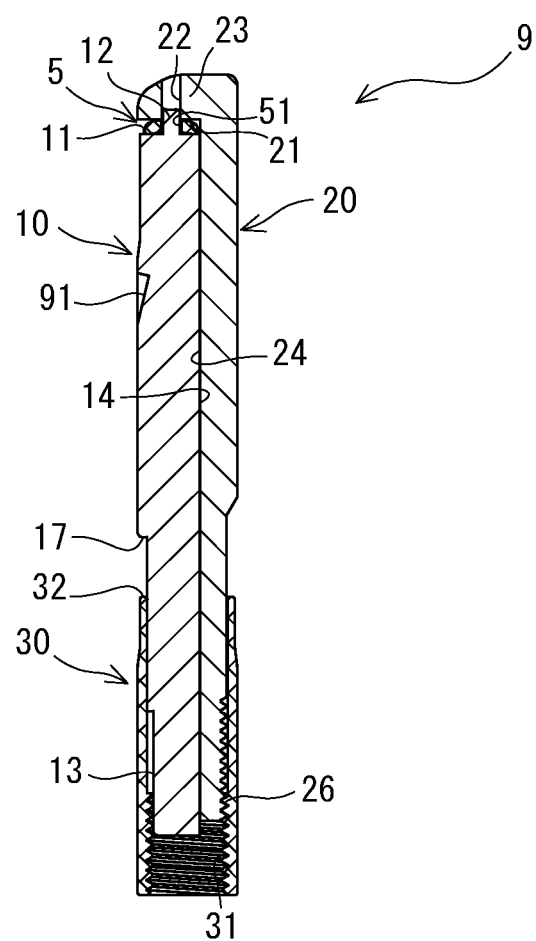
FIG. 15 is a sectional explanatory view for explaining another embodiment of the bending tool of the bone plate of the present invention.

As shown in FIG. 15, the bone plate bending tool 9 may not be provided with the urging means (coil spring 40). In that case, to help the operator temporarily hold the bone plate 5 (before the bone plate 5 is held by the pinching force by the sandwiching holding mechanism 3), in addition to knurling to be applied to the peripheral surface of the first member 10, it is possible to provide the first member 10 with a concave portion 91 to easily perform an operation of urging the first member 10 in a direction in which the first sandwiching surface 11 and the second sandwiching surface 21 approach to each other.

The tool of the present invention for bending bone plate is as described below.
(1) A tool for bending a bone plate having a through-hole comprising;
a substantially rod-shaped first member having a first sandwiching surface on a front end surface of said first member;
a substantially rod-shaped second member, which slides along a side part of said first member and has a second sandwiching surface positioned in front of said first sandwiching surface and opposed to said first sandwiching surface,
a connection tubular member connected to said second member and enclosing a peripheral surface of said first member,
a projection provided on one of said first sandwiching surface and said second sandwiching surface, and said projection is capable of inserting into said through-hole of said bone plate and does not prevent said bone plate from being pinchingly sandwiched between said first sandwiching surface and said second sandwiching surface,
wherein said connection tubular member is axially movable on said peripheral surface of said first member in a state said second member being disposed on said side part of said first member, said connecting tubular member that has moved forward in an axial direction restricts an expansion between said first sandwiching surface and said second sandwiching surface, and
said first sandwiching surface and said second sandwiching surface, in cooperation with said connecting tubular member that has moved forward in said axial direction, pinchingly sandwich and immovably hold a peripheral edge of said through-hole of said bone plate into which said projection has inserted.

Therefore, during the bending processing of the bone plate, it is possible to prevent slippage and dropout of the bone plate and thus, improve the bending processability of the bone plate. Further, it is possible to restrain the distortion of the through-hole owing to the holding of the vicinity of the through-hole of the bone plate by the pinching force of the first and second sandwiching surfaces and the projection which has penetrated into the through-hole. Thus, it is possible to improve the bending processability of the bone plate.

The above-described embodiment may also be as described below.
(2) A tool for bending a bone plate according to above (1), wherein one of said first sandwiching surface and said second sandwiching surface has a hole portion capable of accommodating said projection.
(3) A tool for bending a bone plate according to above (1) or (2), comprising an urging means for urging said first member or/and said second member in a direction in which said first sandwiching surface and said second sandwiching surface approach to each other.
(4) A tool for bending a bone plate according to any one of above (1) through (3), wherein said connection tubular member has a contact portion which contacts said first member by said axially moving said connecting tubular member, and said contact portion contacted said first member restrict an expansion between said first sandwiching surface and said second sandwiching surface.
(5) A tool for bending a bone plate according to any one of above (1) through (4), wherein said second member has a second member-side threadedly engaging portion provided at an outer side surface of a rear end portion of said second member, said connection tubular member has a tubular member-side threadedly engaging portion which is provided at an inner surface of said connection tubular member and screws with said second member-side threadedly engaging portion, and said connecting tubular member moves toward a distal end of said first member by rotating said connecting tubular member in a predetermined direction.
(6) A tool for bending a bone plate according to any one of above (1) through (5), wherein said projection is insertable into said through-hole of said bone plate including an inner thread groove.

The tool of the present invention for bending bone plate is as described below.
(7) A tool for bending a bone plate having a through-hole comprising;
a substantially rod-shaped first member having a first sandwiching surface on a front end surface of said first member;

a substantially rod-shaped second member, which slides along a side part of said first member and has a second sandwiching surface positioned in front of said first sandwiching surface and opposed to said first sandwiching surface, a connection tubular member connected to said second member and enclosing a peripheral surface of said first member, a projection provided on one of said first sandwiching surface and said second sandwiching surface, and said projection is capable of inserting into said through-hole of said bone plate and does not prevent said bone plate from being pinchingly sandwiched between said first sandwiching surface and said second sandwiching surface, wherein said second member has a second member-side threadedly engaging portion provided at an outer side surface of a rear end portion of said second member, said connection tubular member has a tubular member-side threadedly engaging portion which is provided at an inner surface of said connection tubular member and screws with said second member-side threadedly engaging portion, and said connecting tubular member moves toward a distal end of said first member by rotating said connecting tubular member in a predetermined direction, said connection tubular member has a contact portion which contacts said first member when moved toward said distal end of said first member by rotating said connecting tubular member in a predetermined direction, and said contact portion contacted said first member restrict an expansion between said first sandwiching surface and said second sandwiching surface.

Therefore, during the bending processing of the bone plate, it is possible to prevent slippage and dropout of the bone plate and thus, improve the bending processability of the bone plate. Further, it is possible to restrain the distortion of the through-hole owing to the holding of the vicinity of the through-hole of the bone plate by the pinching force of the first and second sandwiching surfaces and the projection which has penetrated into the through-hole. Thus, it is possible to improve the bending processability of the bone plate.

The set of the tool of the present invention for bending the bone plate is as described below.

(8) A set of a tool for bending a bone plate comprising a tool for bending said bone plate according to any one of above (1) through (7) and a gripping tool having a gripping portion capable of gripping said bone plate at a portion other than a portion where said bone plate is pinchingly held by said bone plate bending tool and a substantially rod-shaped main body.

Therefore, during the bending processing of the bone plate, it is possible to prevent slippage and dropout of the bone plate and thus, improve the bending processability of the bone plate. Further, it is possible to restrain the distortion of the through-hole owing to the holding of the vicinity of the through-hole of the bone plate by the pinching force of the first and second sandwiching surfaces and the projection which has penetrated into the bone plate. Thus, it is possible to improve the bending processability of the bone plate. Further, the sandwiching of the bone plate owing to the first sandwiching surface and the second sandwiching surface and the projection of the bone plate which have penetrated into the through-hole of the bone plate, it is possible to improve the bending processability of the bone plate. Further, by using the bending tool and the gripping tool, it is possible to apply a large bending force (bending moment) by utilizing the lever principle. Thereby it is possible to bend the bone plate by using a smaller force.

The method for bending the bone plate is as described below:

(9) Method for bending a bone plate using said bone plate bending tool according to any one of above (1) through (7) including, preparing said bone plate bending tool;

allowing said projection of said bone plate bending tool to insert to said through-hole of said bone plate;

holding and pinching said bone plate between said first sandwiching surface and said second sandwiching surface; and curvingly deforming said bone plate at portions other than a portion where said bone plate is pinchingly held between said first and second sandwiching surfaces with said bone plate being gripped with an operator's hand or a jig.

Therefore, during the bending processing of the bone plate, it is possible to prevent slippage and dropout of said bone plate and thus, improve the bending processability of the bone plate. Further, it is possible to restrain the distortion of the through-hole owing to the holding of the vicinity of the through-hole of the bone plate by the pinching force of the first and second sandwiching surfaces and the projection which has penetrated into the through-hole. Thus, it is possible to improve the bending processability of the bone plate.

The above-described embodiment may also be as described below.

(10) A method for bending a bone plate according to above (9), wherein said bone plate bending tool has said projection which is insertable to said through-hole of said bone plate; and one of said first and second sandwiching surfaces has a hole portion capable of accommodating said projection projecting from said through-hole.

What is claimed:

1. A tool for bending a bone plate having a through-hole comprising;
   a first rod-shaped member having a first surface provided at a front end of said first rod-shaped member,
   a second rod-shaped member having a second surface opposed to said first surface of said first rod-shaped member and sandwiching said bone plate between said first surface of said first rod-shaped member and said second surface of said second rod-shaped member,
   a connection tubular member connected to said second rod-shaped member,
   wherein said first rod-shaped member or said second rod-shaped member has a projection provided on one of said first surface and said second surface and being capable of insertion into said through-hole of said bone plate,
   said second rod-shaped member is positioned on a side of said first rod-shaped member and is slidable in the axial direction of said first rod-shaped member, and
   said connection tubular member encloses rear end portions of said first rod-shaped member and said second rod-shaped member and is rotatable around a central axis of said connecting tubular member.

2. A tool for bending a bone plate according to claim 1, wherein one of said first surface of said first rod-shaped member and said second surface of said second rod-shaped member has said projection, and the other of said first surface of said first rod-shaped member and said second surface of said second rod-shaped member has a hole capable of accommodating and opposed to said projection.

3. A tool for bending a bone plate according to claim 1, comprising an accommodation concave portion opening toward said second rod-shaped member and rearward at a rear end portion of said first rod-shaped member which projects toward said first rod-shaped member, and a coil spring positioned on said lower projected portion in said accommodation concave portion of said first rod-shaped member.

4. A tool for bending a bone plate according to claim 1, wherein a rear end portion of said first rod-shaped member is set smaller in its diameter than a central portion of said first rod-shaped member, and a stepped portion is formed at the boundary between a rear end portion of said first rod-shaped member and a central portion of said first rod-shaped member, and
- a front-end surface of said connection tubular member is formed as a contact portion capable of contacting said stepped portion of said first rod-shaped member and prevent a rearward movement of said first rod-shaped member.

5. A tool for bending a bone plate according to claim 1, wherein
- said second rod-shaped member has a second rod-shaped member-side threadedly engaging portion provided at an outer side surface of a rear end portion of said second rod-shaped member,
- said connection tubular member has a tubular member-side threadedly engaging portion which is provided at an inner surface of said connection tubular member and screws with said second rod-shaped member-side threadedly engaging portion, and
- said connecting tubular member moves toward a front end of said tool for bending a bone plate by rotating around a central axis of said connecting tubular member.

6. A set of a tool for bending a bone plate comprising, said tool for bending a bone plate according to claim 1 and a gripping tool,
- wherein said gripping tool has a rod-shaped main body and a gripping portion provided to said rod-shaped main body and capable of gripping said bone plate at a portion other than a portion where said bone plate is sandwiched between said first surface of said first rod-shaped member and said second surface of said second rod-shaped member.

7. A tool for bending a bone plate having a through-hole comprising;
- a first rod-shaped member having a first surface provided at a front end of said first rod-shaped member,
- a second rod-shaped member having a second surface opposed to said first surface of said first rod-shaped member and sandwiching said bone plate between said first surface of said first rod-shaped member and said second surface of said second rod-shaped member,
- a connection tubular member connected to said second rod-shaped member and enclosing rear end portions of said first rod-shaped member and said second rod-shaped member,
- wherein said first rod-shaped member or said second rod-shaped member has a projection provided on one of said first surface and said second surface and being capable of insertion into said through-hole of said bone plate,
- said second rod-shaped member is positioned on a side of said first rod-shaped member and is slidable in the axial direction of said first rod-shaped member,
- said second rod-shaped member has a second rod-shaped member-side threadedly engaging portion provided at an outer side surface of a rear end portion of said second rod-shaped member,
- said connection tubular member has a tubular member-side threadedly engaging portion which is provided at an inner surface of said connection tubular member and screws with said second rod-shaped member-side threadedly engaging portion, and
- said connecting tubular member moves toward a front end of said tool for bending a bone plate by rotating around a central axis of said connecting tubular member.

* * * * *